United States Patent [19]

Manner et al.

[11] Patent Number: 5,019,659

[45] Date of Patent: May 28, 1991

[54] METHOD OF SEPARATING 2-NITROSOPHENOL ISOMER FROM ADMIXTURE WITH 4-NITROSOPHENOL ISOMER

[75] Inventors: James A. Manner, Monroeville; Charles H. Hoelscher, Murrysville, both of Pa.

[73] Assignee: PPG Industries, Inc., Pittsburgh, Pa.

[21] Appl. No.: 569,115

[22] Filed: Aug. 17, 1990

Related U.S. Application Data

[63] Continuation-in-part of Ser. No. 383,121, Jul. 20, 1989, abandoned.

[51] Int. Cl.$^5$ ............................................. C07C 207/00
[52] U.S. Cl. ..................................... 568/949; 568/706; 568/708
[58] Field of Search .................... 568/706, 708, 949

[56] References Cited

U.S. PATENT DOCUMENTS

| 2,245,945 | 6/1941 | van Dijck et al. | 568/708 X |
| 2,419,976 | 5/1947 | Trepagnier et al. | 568/949 |
| 3,668,261 | 6/1972 | Harvey et al. | 568/706 |
| 3,894,096 | 7/1975 | Whitten | 568/708 |
| 3,917,719 | 11/1975 | Baldwin et al. | 568/708 |
| 3,980,717 | 9/1976 | Subluskey | 568/708 |
| 4,232,175 | 11/1980 | Smith et al. | 568/706 |
| 4,371,721 | 2/1983 | Wu | 568/750 |
| 4,816,584 | 3/1989 | Kwak et al. | 544/71 |
| 4,909,963 | 3/1990 | Kwak et al. | 252/586 |
| 4,936,995 | 6/1990 | Kwiatkowski | 252/586 |

OTHER PUBLICATIONS

Organic Synthesis, Collective vol. I, Henry Gilman, Ed. John Wiley & Sons, Inc. N.Y., 1932, pp. 411–412.
"A New Chemical Reaction with the Nitrosyl Radical NOH", O. Baudisch, Science, vol. 92, pp. 336–337 (1940).
"Preparation of O-Nitrosophenols from Benzene or Other Aromatic Hydrocarbons at Room Temperature", O. Baudisch, J. Amer. Chem. Soc., 63, 622 (1941).
"O-Nitrosophenols I & II", A. Cronheim, J. Org. Chem., 12, pp. 1–6 and 7, 14, 17–18 (1947).

Primary Examiner—John S. Maples
Assistant Examiner—Chhaya Sayala
Attorney, Agent, or Firm—Edward J. Whitfield; Irwin M. Stein

[57] ABSTRACT

Disclosed is a method for selectively separating 2-nitrosophenol from an isomeric mixture containing 2-nitrosophenol and 4-nitrosophenol by contacting the mixture with an organic solvent so as to preferentially dissolve the 2-nitrosophenol from the mixture.

8 Claims, No Drawings

METHOD OF SEPARATING 2-NITROSOPHENOL ISOMER FROM ADMIXTURE WITH 4-NITROSOPHENOL ISOMER

CROSS-REFERENCE TO RELATED APPLICATION

This application is a continuation-in-part of copending application Ser. No. 07/383,121, filed July 20, 1989, now abandoned.

BACKGROUND OF THE INVENTION

Spiro(indolino)benzoxazine or spiro(benzindolino)-benzoxazine photochromic compounds may be prepared by condensing a nitrosophenol compound with an indoline (Fischer's base) or indolium salt, e.g., iodide salt, as described, e.g., in U.S. Pat. Nos. 4,816,584, and 4,936,995.

In order to improve the yield of spiro(indolino) type photochromic compounds, e.g., of the type described in U.S. Pat. No. 4,816,584, the substituted or unsubstituted indoline or indolium salt should be reacted with nitrosophenol, e.g., 3,5-dimethoxy-2-nitrosophenol, containing as little as possible of isomers, e.g., 3-5-dimethoxy-4-nitrosophenol, that do not produce photochromic compounds.

However, the typically used methods of making, e.g., 3,5-dimethoxy-2-nitrosophenol, also may result in co-production of substantial amounts, i.e., up to about 70 weight percent, and typically from about 35 to 50 weight percent of 3,5-dimethoxy-4-nitrosophenol, necessitating selective separation of the 2-nitrosophenol (ortho) isomer from admixture with the 4-nitrosophenol (para) isomer to obtain 2-nitrosophenol isomer of sufficient purity to produce acceptable yields of photochromic compound.

One such method of selectively separating the 2-nitrosophenol isomer from admixture with the 4-nitrosophenol isomer is described by Cronheim, J. Org. Chem., 12, 1, 7 & 20 (1947) wherein the 2-nitrosophenol isomer is selectively complexed with copper salts. However, attempts to duplicate this technique have not been successful.

In accordance with this invention, a straightforward, convenient, readily reproducible method has been found for preferentially dissolving 2-nitrosophenol (ortho) isomer from a mixture of 2-nitrosophenol and 4-nitrosophenol (para) isomers, which method enables isolation of 2-nitrosophenol isomer of at least 90 percent purity.

THE INVENTION

In accordance with this invention, 2-nitrosophenol is selectively separated from an isomeric mixture containing 2-nitrosophenol and 4-nitrosophenol by slurrying the mixture with an organic solvent which preferentially dissolves the 2-nitrosophenol (ortho) isomer from the isomeric mixture. Following solvent removal, 2-nitrosophenol having a purity of at least 90 percent is obtained.

Numerous organic solvents have been tested, and among those found more practicable for use in accordance with this invention, generaly include those having relatively low polarity, a low water miscibility and a dielectric constant up to about 10. Some such solvents include chloroform, chlorobenzene, butyl chloride, ethyl acetate, methylethyl ketone, toluene and tetrahydrofuran. Other somewhat more polar solvents found useful in the practice of the invention include acetonitrile, acetone and 2-pentanone.

Organic solvents particularly preferred for use in the practice of this invention are acetone, acetonitrile, chlorobenzene and chloroform. Mixtures of suitable solvents may, of course also be used.

Solvent extraction of the 2-nitrosophenol and 4-nitrosophenol isomer mixture can be conducted from room temperature (i.e., about 23° C.) up to reflux temperature of the solvent using sufficient solvent for a time sufficient to preferably dissolve the 2-nitrosophenol isomer from the mixture. The quantity of solvent used is not particularly critical, sufficient solvent being used to maintain a workable and handleable slurry. Typically, at least about 2 parts by weight of solvent per part by weight of nitrosophenol isomer mixture should provide a satisfactory result. After extraction, the 2-nitrosophenol isomer may be isolated from the solvent by any suitable techniques, e.g., crystallization or by evaporation of the solvent.

The invention is further illustrated but is not intended to be limited by the following Examples.

EXAMPLE 1

To a nitrogen purged 500 ml four-necked round bottomed flask equipped with a thermometer, motor driven Teflon ® blade paddle stirrer and nitrogen inlet was added 30.8 g (0.20 mole) of 3,5-dimethoxyphenol (DMP), 95 g of acetic acid and 30 g of distilled water. The mixture was stirred at room temperature for 30 min. to dissolve all of the phenol then cooled to 0° C. using an ice-water-sodium chloride bath. To this vigorously stirred mixture (600 rpm) was added dropwise a solution of 14.2 g (0.20 mole) of $NaNO_2$ in 20 ml of water over 25 min. while maintaining the temperature around 0° to 2° C. The acetic acid solution turned a red color immediately on addition of sodium nitrite and eventually became a red slurry near the end of the addition. After addition, a small sample was withdrawn and analyzed by HPLC.

The ice bath was then removed and the mixture stirred for 60 min. (temperature rose to 12° C.) during which time a sample was withdrawn (+50 min.) for HPLC analysis. The HPLC analysis employed a Varian 5000 liquid chromatograph set at a flow rate of between 1.0 and 1.5 milliliters per minute, a Zorbax ODS column (4.6 mm×25 cm) and a solvent system of 70/30 V/V acetonitrile/water containing about 0.05 weight percent phosphoric acid. The thick red slurry (56% ortho, 44% para by HPLC) was then poured onto a medium porosity glass frit to remove most of the acetic acid (about 40 min. filtration using house vacuum). The residue in the flask was slurried with 100 ml of acetonitrile and analyzed by HPLC and found to contain 85/15 area % of ortho/para isomers. This result led to slurrying the remaining red cake on a medium porosity glass frit with acetonitrile followed by slight suction to obtain a filtrate high in 3,5-dimethoxy-2-nitrosophenol.

In a separate experiment with the crude material, 57 g was transferred to an Erlenmeyer flask along with 200 g of acetonitrile. The mixture was stirred and heated to 55° to 62° C. for 45 min. and then poured onto a medium porosity frit. The filtrate contained high purity (>90%) 3,5-dimethoxy-2-nitrosophenol.

Solvent was removed from the filtrate fractions by thin film rotary evaporation affording a total of 23.0 g (62.7% overall yield) of 93% pure 3,5-dimethoxy-2-nitrosophenol.

EXAMPLE 2

To a 12 liter reactor were charged 1573.4 g (10 mole) of DMP (melted in oven at 70° C.), 4750 g of acetic acid and 1500 g of water. Using a larger ice-salt-water bath, the mixture was cooled to 3.5° C. after which 711.2 g (10 mole) of sodium nitrite in 1000 ml of water was added over 4.2 hr. (reaction temp. range 4° to 7° C.). After 1 hr. the rpm of the stirrer were increased to 800 and then to 900 after 2 hr. to keep the thick mixture stirring at a reasonable rate.

The ice water was removed from the bath and the mixture stirred overnight (18 hr.) at 600 rpm and allowed to warm to room temperature. The crude red cake (64% ortho, 36% para by HPLC) was filtered through glass frits, washed with water in the funnels or in large plastic beakers. The ortho isomer was separated from the crude cake by slurry extraction, one-half of the cake being extracted with acetonitrile and acetone being used to extract the other half of the cake.

Solvent was removed from the filtrate fractions by thin film rotary evaporation affording a total of 1178.8 g (64.3% overall yield) of 93% pure 3,5-dimethoxy-2-nitrosophenol.

EXAMPLE 3

About 2.5 grams of a substantially equimolar mixture of 3,5-dimethoxy-2-nitrosophenol and 3,5-dimethoxy-4-nitrosophenol were equilibrated with about 50 milliliters of various organic solvents. About 5 milliliter portions of the equilibrated isomer mixtures were withdrawn and filtered through a 5 micron syringe filter to remove undissolved solids. The filtrates were added to tared vials and the contents analyzed by HPLC using a Varion 5000 liquid chromatograph set at 1.5 milliliters per minute and provided with a 2050 UV detector and set at a wavelength of 310 nanometers. A DuPont C L-8086 column was used with a solvent system consisting of 60/40 V/V methanol water containing about 1.0 weight percent phosphoric acid. The percent isomer distribution of the filtered material using the various solvents as an extractant was determined to be as follows:

| SOLVENT | 2-ISOMER | 4-ISOMER |
|---|---|---|
| Chloroform | 97.45 | 2.55 |
| Acetone | 93.78 | 6.15 |
| Ethyl Acetate | 93.46 | 4.42 |
| Methylene Chloride | 98.16 | 1.52 |
| Chlorobenzene | 92.80 | 2.80 |
| Acetonitrile | 95.93 | 1.57 |
| Butyl Chloride | 92.89 | 4.71 |
| Methylethyl Ketone | 89.93 | 10.05 |
| 2-Pentanone | 88.54 | 11.30 |
| Tetrahydrofuran | 94.28 | 5.72 |
| Toluene | 83.48 | 15.94 |

EXAMPLE 4

A number of other solvents were screened to determine their ability to selectively solubilize either the 2-nitrosophenol isomer or the 4-nitrosophenol isomer. To about 2 milliliters of each solvent in a 1 dram (3.7 cc) bottle was added about 0.05 gram of the solid 2- and 4-nitrosophenol isomer mixture prepared as described in Example I. The results of this experiment are as follows:

| SOLVENT | PERCENT SOLUBLE | |
|---|---|---|
| | 2-isomer | 4-isomer |
| Water | 36 | 64 |
| Dilute Ammonium Hydroxide | 100 | 100 |
| 2-amino-2-methy-1-propanol | 100 | 100 |
| Triethanolamine | <10 | <10 |
| Pyridine | 100 | 100 |
| Diethylene glycol | 100 | 100 |
| Perchloroethylene | 60 | 40 |
| N-methylpyrrolidone | 100 | 100 |
| Dimethyl Formamide | 100 | 100 |
| Dioxane | 78 | 22 |
| Pentachlorethane | 8.5 | 91.4 |
| Dimethylcarbonate | 38 | 62 |
| Diethylcarbonate | 38 | 62 |
| i-propanol | 57 | 43 |
| n-butanol | 63 | 37 |
| Methanol | 55 | 45 |

As shown by the foregoing Examples the process of the invention provides a straightforward, expedient means for separating 2-nitrosophenol from a mixture contianing 2-nitrosophenol and 4-nitrosophenol. Numerous solvents have been tested for suitability for use in accordance with the invention and other solvents not specifically enumerated herein may be found suitable by those skilled in the art that preferentially dissolve 2-nitrosophenol for admixture with 4-nitrosophenol using the techniques described herein or any other suitable technique.

We claim:

1. A process for separating 2-nitrosophenol from an isomeric mixture containing 2-nitrosophenol and 4-nitrosophenol by contacting the mixture with an organic solvent cabable of preferentialy solubilizing the 2-isomer, said solvent selected from acetone, acetonitrile, chlorobenzene, chloroform, butyl chloride, ethyl acetate, methylethyl ketone, tetrahydrofuran, 2-pentanone, toluene or mixtures thereof, said solvent being used in sufficient quantity and for a time sufficient to preferentially dissolve 2-nitrosophenol from the isomeric mixture.

2. The process of claim 1 including the step of isolating the 2-nitrosophenol from the organic solvent.

3. The process of claim 2 wherein isolation of the 2-nitrosophenol is effected by evaporating the solvent.

4. The process of claim 1 wherein the isomeric mixture is contacted with organic solvent at a temperature ranging from ambient up to reflux temperature of the solvent.

5. The process of claim 1 wherein the solvent is selected from acetone or acetonitrile.

6. The process of claim 5 wherein the solvent is acetonitrile.

7. The process of claim 1 wherein the solvent is selected from one having a dielectric constant of not more than about 10.

8. The process of claim 7 wherein the solvent is selected from chlorobenzene or chloroform.

* * * * *